(12) United States Patent
Hall et al.

(10) Patent No.: US 6,418,876 B1
(45) Date of Patent: Jul. 16, 2002

(54) METHOD AND AN APPARATUS FOR MONITORING AN ANIMAL

(75) Inventors: Robert Christopher Hall, Knebworth; Diane S. Spencer, Flitwick; Michael J. Street, Bedford, all of (GB)

(73) Assignee: Alfa Laval Agri AB, Tumba (SE)

( * ) Notice: Subject to any disclaimer, the term of this patent is extended or adjusted under 35 U.S.C. 154(b) by 0 days.

(21) Appl. No.: 09/446,997

(22) PCT Filed: Jul. 2, 1998

(86) PCT No.: PCT/SE98/01305

§ 371 (c)(1),
(2), (4) Date: Feb. 3, 2000

(87) PCT Pub. No.: WO99/01026

PCT Pub. Date: Jan. 14, 1999

(30) Foreign Application Priority Data

Jul. 2, 1997 (SE) ................................ 9702558
Jul. 2, 1997 (SE) ................................ 9702559

(51) Int. Cl.⁷ ................................ A01J 3/00; A01J 5/00
(52) U.S. Cl. .................... 119/14.08; 119/421
(58) Field of Search ................ 119/14.08, 14.01, 119/14.02, 14.03, 417, 416, 421

(56) References Cited

U.S. PATENT DOCUMENTS

| 3,911,899 A | 10/1975 | Hattes |
| 4,726,322 A | 2/1988 | Torsius |
| 4,830,022 A | 5/1989 | Harshe et al. |
| 5,069,160 A | 12/1991 | Street et al. |
| 5,107,845 A | 4/1992 | Guern et al. |
| 5,816,190 A | * 10/1998 | van der Lely ........... 119/14.08 |
| 5,878,692 A | * 3/1999 | Ornerfors ................. 119/14.08 |
| 5,979,359 A | * 11/1999 | Hansson .................... 119/14.08 |

FOREIGN PATENT DOCUMENTS

| CA | 1296068 | 2/1992 |
| CH | 1648367 | 5/1991 |
| DE | 4229073 | 3/1994 |
| EP | 0178197 | 4/1986 |
| EP | 0406978 | 1/1991 |
| EP | 0549081 | 6/1993 |
| EP | 0705536 | 4/1996 |
| EP | 0743043 | 11/1996 |
| EP | 0808567 | 11/1997 |
| GB | 2240392 | 7/1991 |
| GB | 2254691 | 10/1992 |
| GB | 2260196 | 4/1993 |
| SE | 9504707 | 6/1997 |
| WO | WO 91/00054 | 1/1991 |
| WO | WO 94/16620 | 8/1994 |
| WO | WO 94/20021 | 9/1994 |

* cited by examiner

Primary Examiner—Charles T. Jordan
Assistant Examiner—Judith A. Nelson
(74) Attorney, Agent, or Firm—Weingarten, Schurgin, Gagnebin & Lebovici LLP

(57) ABSTRACT

An apparatus and a method are provided for monitoring an animal and having a controller. According to a first aspect of the apparatus and method, the controller has a sensor adapted to sense a movement rate of the animal and to establish a value of the movement rate regarding the animal. According to a second aspect of the apparatus and method, the controller includes a sensor provided to allow establishment of the existence of the breath of the animal, and a heart rate calculation device for establishing a value of the breathing rate regarding the animal.

15 Claims, 5 Drawing Sheets

METHOD AND AN APPARATUS FOR MONITORING AN ANIMAL

TECHNICAL FIELD

The present invention relates to an apparatus and a method for monitoring an animal.

OBJECT OF THE INVENTION

Wherever a herd of cows is to be monitored—indoors or outdoors—there is a need for establishing the behaviour or the state of health of each cow. Generally, this is performed by the milker at each milking session. This, however, is not a very precise method, as an early stage of heat, a nervous behaviour, illness or diseases, such as BSE ("mad cow's disease") does not necessarily appear during milking session, but during times of the day, when the milker is not present. Accordingly, there is a need for early establishment of an abnormal behaviour or state of health of the animal, especially at farms with large herds.

It is, accordingly, an object of the present invention to provide a method and an apparatus for allowing monitoring of the animal in order to allow early establishment of an abnormal state of health or an abnormal behaviour of the animal.

SUMMARY OF THE INVENTION

This has been solved by an apparatus of the initially defined kind, characterised in that it comprises a control means having a sensor means adapted to sense a movement of the animal and to establish a value of the movement regarding said animal, said control means being adapted to provide an output signal.

It has furthermore been solved by an apparatus of the initially defined kind, which is characterised in that it comprises control means having sensor means for establishing the existence of a breathing of the animal, and heart rate calculation means for establishing a value of the breathing rate regarding said animal, said control means being adapted to provide an output signal.

It has also been solved by a method of the initially defined kind, which is characterised by sensing the existence of a breathing of the animal by means of a breathing sensor associated with a control means, and by establishing the breathing rate regarding said animal.

By the said apparatus and method, it is possible to promptly take care of an animal and perform appropriate actions.

Suitably, said control means is adapted to provide said output signal in case said value of the movement exceeds a predetermined level and not to provide said signal in case said value of the movement does not exceed said predetermined level, in order to allow certain movement of the animal.

Alternatively, said control means is adapted to provide said output signal in case the said value exceeds a predetermined level and not to provide said signal in case said value does not exceed said predetermined level.

Hereby, it is possible to determine or to set a limit to said value.

Preferably, the value of the movement rate is stored at a plurality of or at variable occasions regarding said animal. Alternatively, the value of the breathing rate is stored at a plurality of or at variable occasions regarding said animal Hereby, it is possible to more extensively monitor an animal suspected to behave in an abnormal manner.

Suitably, said control means is adapted to establish an average movement rate or an average breathing rate regarding said animal. outgoing from the stored values. Hereby, a normal state of health or behaviour is possible to establish.

Preferably, said sensor means comprises a non-invasive sensor. Hereby, it is possible to sense the movement or the breathing of the animal without hurting it.

Such a sensor may be adapted to be held against a part of the animal's body, e.g. its belly and could be a tactile sensor.

Alternatively, said sensor means is adapted to be held at a distance from the animal's body, such as a laser sensor, an ultrasonic sensor. an ultrasonic distance meter, provided in the vicinity of the animal's belly, a microphone provided in the vicinity of the animal's head or a camera associated with said control means for allowing image processing of a received image.

Additionally, the apparatus comprises an animal related apparatus adapted to perform an animal related operation to an animal, said control means being associated with said animal related apparatus, wherein said animal related means is adapted to perform an action in response to said output signal.

Hereby, it is possible to control the animal related apparatus to perform a suitable action, if e.g. an abnormal behaviour or state of health of the animal is indicated. Such action may be to at least suspend said animal related operation in case already started and not to initiate said operation in case not started.

Preferably, said animal related apparatus is an automatic milking apparatus comprising a robot arm for performing said animal related operation, said control means being associated with said robot arm. Accordingly, said animal related operation is at least one of inspecting the teats, spraying the teats, cleaning the teats and attaching teatcups to the teats of the animal.

Suitably, said sensor is provided to sense an animal in an animal space, such as a milking stall, a feeding stall or a gateway provided with sideward limiting means.

Preferably, said animal space is provided with at least one gate, said control means being associated with said gate, and wherein said animal related operation is to open said gate for allowing the animal to leave the animal space. Hereby, it is possible to prevent an animal, which behaves in an abnormal way, from destroying e.g. the milking equipment or a robot arm.

Suitably, an identification means is provided, for allowing values of rates regarding an identified animal individual to be evaluated. Hereby, it is possible to monitor each animal individual of a whole herd.

Preferably, said control means is associated with an alerting means, to which the control means is adapted to send an output signal. Hereby, it is possible to promptly call for the milker by ringing a bell, a buzzer, sending a signal to a mobile telephone or via the Internet to a service man.

Suitably, said sensing means is adapted to provide a value of the distance of said movement. Alternatively, said sensing means is adapted to provide a value of the velocity of said movement. Alternatively, said sensing means is adapted to provide a value of the acceleration of said movement.

Preferably, said sensor means includes a time calculating means for establishment of time elapsed during the animal's movement. Hereby, it is possible to calculate an acceleration outgoing from the sensed values.

Suitably, said sensor is adapted to sense the amplitude of said movement. Alternatively, or additionally, said sensor is adapted to sense the frequency of said movement. Hereby, it is possible to sense whether the animal moves violently or is shivering.

DRAWING SUMMARY

DETAILED DESCRIPTION OF THE INVENTION

Figure 1A:
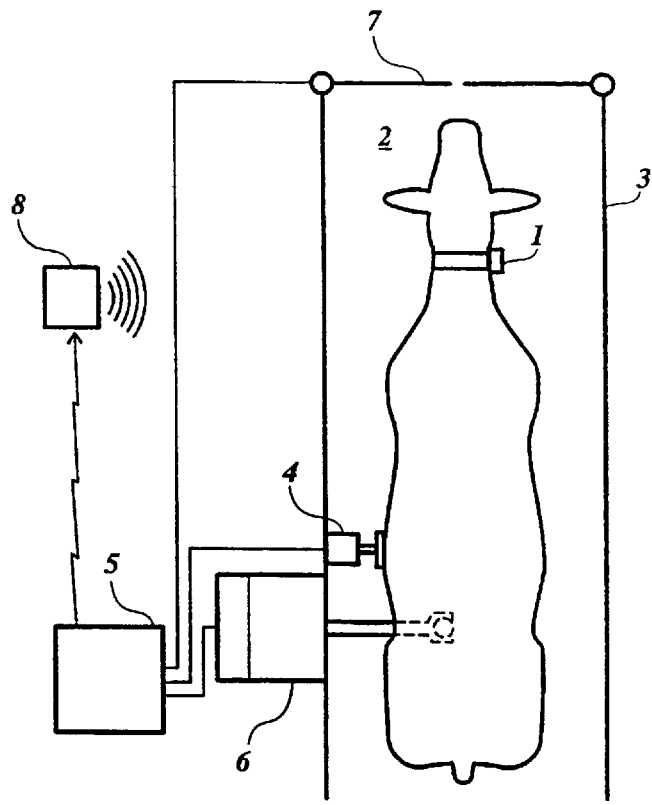
FIGS. 1A and 1B are top views of a cow in an animal space provided with a tactile sensor means touching the body of a cow.

FIG. 1A. shows schematically a cow provided with a transponder 1 for allowing identification of the cow individual. The transponder communicates with a transmitter/receiver (not shown). The cow is in an animal space 2, such as a milking stall, a feeding stall or a gateway, defined at its sides by a sideward limiting means 3, such as a wall or a railing. According to a first embodiment, a movement sensor 4 in the form of a tactile sensor is provided on one side of the animal.

The tactile sensor 4 may be in the form of a hydraulic or pneumatic cylinder (also called air spring) provided with an extension measurement means connected to a control means 5.

The control means 5 calculates the movement rate by taking into account the time elapsed for each breath or a row of breaths.

A milking robot 6 is provided with a robot arm for cleaning the teats, attaching teatcups etc. and is connected to the control means 5. A gate 7 is connected to the control means 5 to keep the cow in the stall or allow her to leave it.

An alerter 8 is connected to the control means 5, preferably, but not necessarily, wirelessly, so that the dairy maid can be made observant of an arisen extraordinary situation. The alerter may be a mobile telephone, a buzzer or a bell.

Figure 1B:
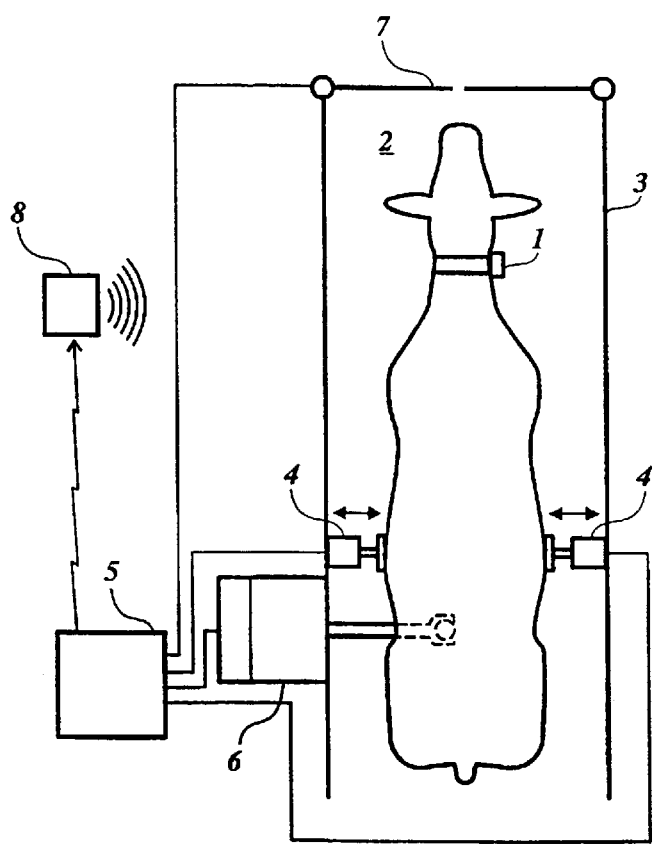

In FIG. 1B, a pair of tactile movement sensors 4 connected to the control means 5 is provided for better resolution, as a pair of sensors 4 will increase the sensing accuracy.

Figure 2A:
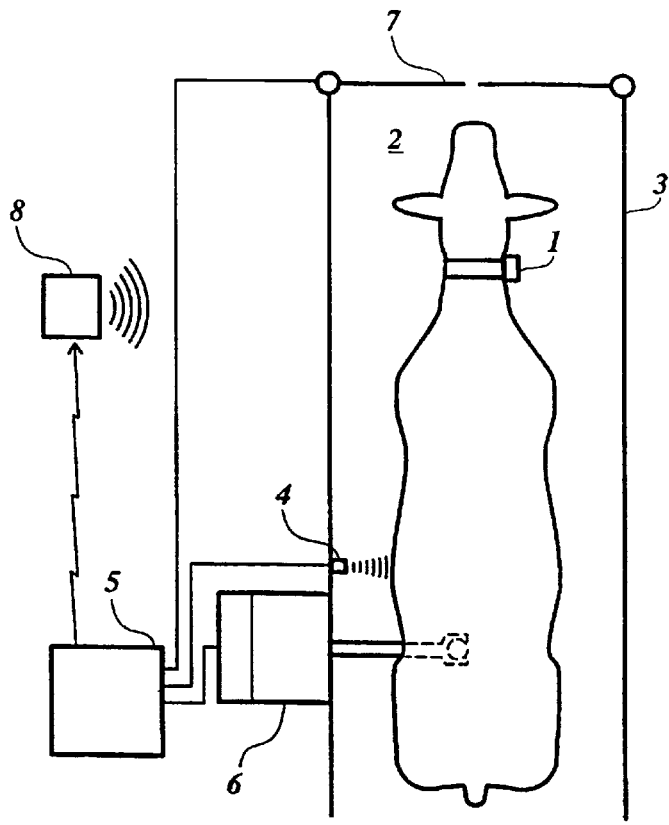
FIG. 2A and 2B are top views of a cow in an animal space provided with a sensor means sensing the body of a cow from a distance.
Figure 2B:
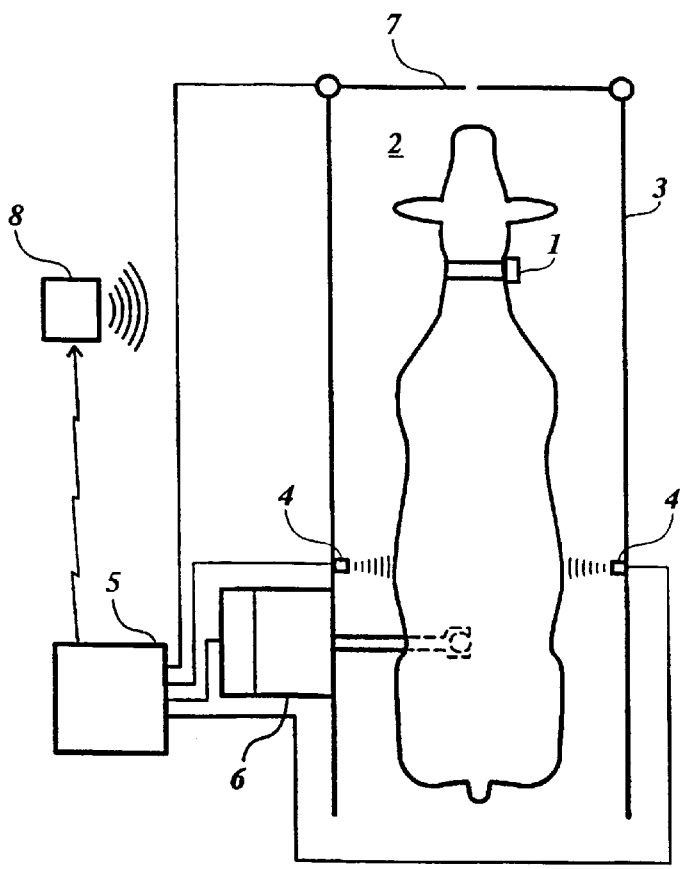

FIG. 2A shows an alternative sensor 4 for sensing the movement of the cow. The sensor 4 is associated with a control means 5. Such a sensor may be an ultrasonic distance meter sensing the time of flight of the sound waves, or a laser distance meter using a triangulation technique. In FIG. 2B, a pair of such breathing sensors 4 are provided for the same reason as in FIG. 1B.

Figure 3:
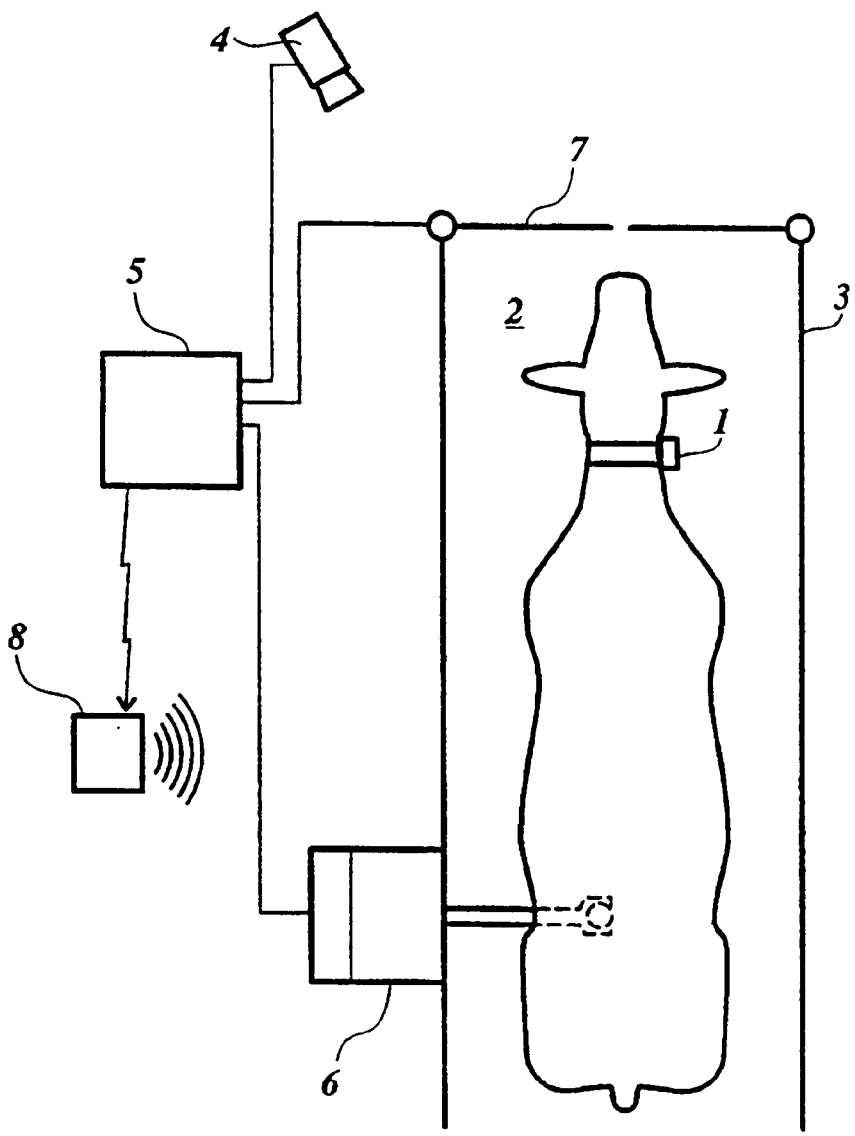
FIG. 3 is a top view of a cow in an animal space provided with viewing means for viewing the cow.

FIG. 3 shows yet an alternative movement sensor 4 comprising viewing means, such as a video camera or a digital camera. The viewing means is connected to the control means 5, which contains image analyzing means. As is the case, regarding the movement sensors described above, the control means 5 is arranged to control the movement of the robot arm and the opening and the closing of the gate 7.

In the following, a second embodiment of the invention will be described.

Figure 4:
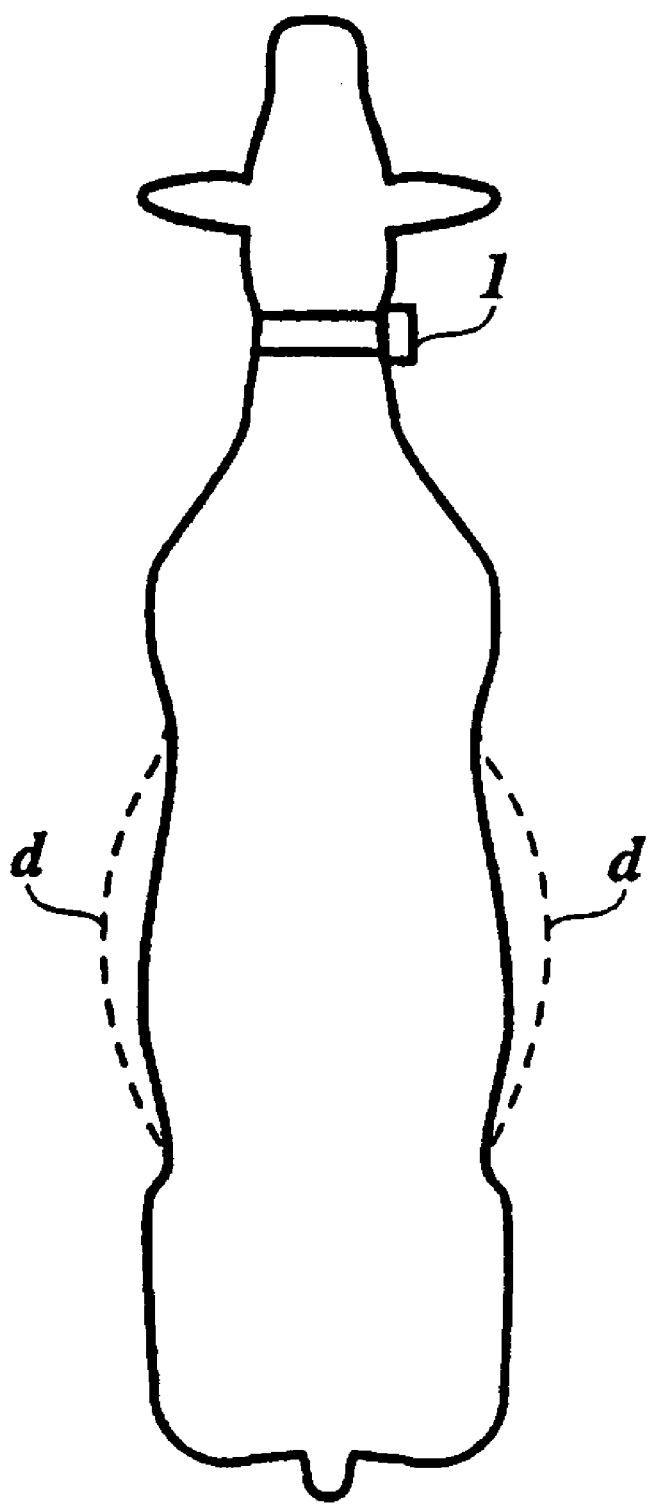
FIG. 4 is a top view of a breathing cow.

FIG. 4. shows schematically a cow as seen from above. Rigid lines indicate the state of her belly after exhalation, whereas the broken lines indicate the state of her belly after inhalation. The difference in displacement of one side of the belly is indicated at d.

What is described in connection with FIGS. 1A, 1B, 2A and 2B is also applicable to the second embodiment however, with the following modifications.

The movement sensor 4 as the tactile sensor shown in FIG. 1A in this embodiment is arranged to sense the displacement d in order to establish an existing breathing of the cow. However, the control means 5 instead calculates the breathing rate by taking into account the time elapsed for each breath or a row of breaths.

The movement sensor 4 including a pair of tactile sensors as shown in FIG. 1B is in this embodiment adapted, together with the control means 5, to establish the total displacement d+d=2d. Also, the movement sensor 4 may be a pair of breathing sensors which will increase the sensing accuracy, as movement of the cow will be possible to take into account.

The sensor means of FIGS. 2A and 2B is used as a breathing sensor 4, which senses the displacement d of the belly from a distance.

Figure 5A:
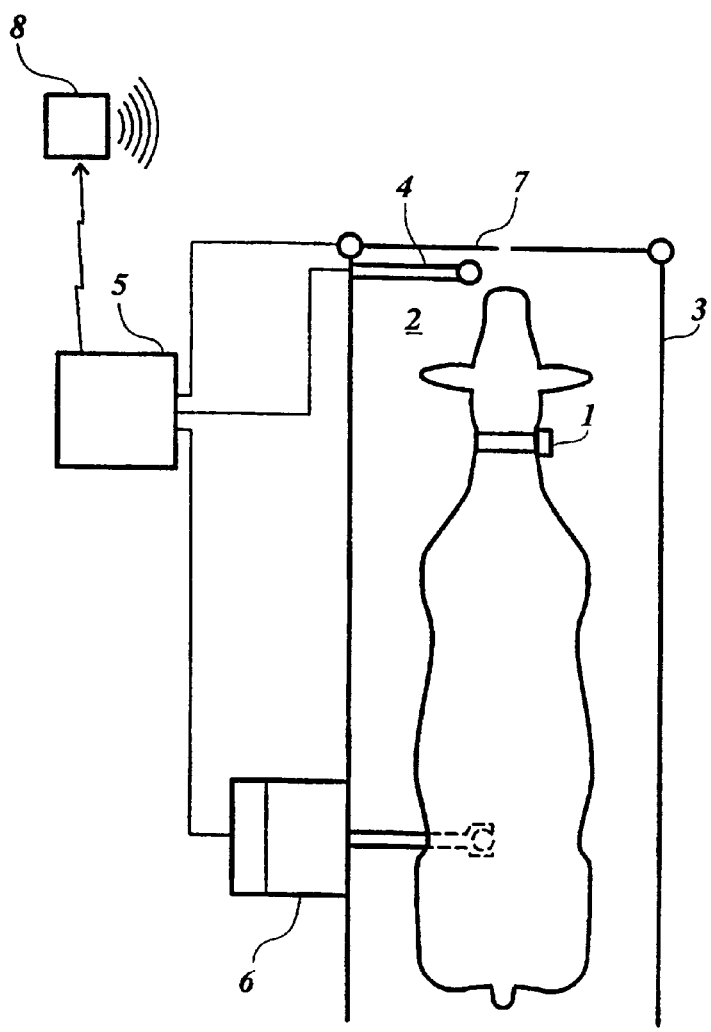
FIGS. 5A and 5B are different views of a cow in an animal space provided with a microphone.

In FIG. 5A, the movement sensor 4 is arranged as a microphone on the sideward limiting apparatus 3, and is directed towards the head, preferably the muzzle of the cow. The direction of the microphone may also be performed electronically. The microphone may be directed to other parts of the cow, e.g. the belly. It is, of course, only possible to establish the breathing rate, not the displacement by means of the microphone.

Figure 5B:
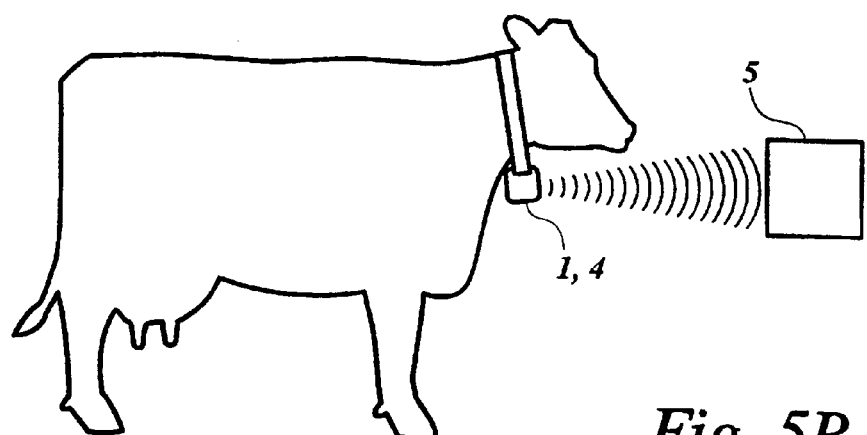

In FIG. 5B, the movement sensor 4 is a microphone integrated with the transponder 1 in a common housing, attached to a collar to be worn by the cow. Of course, the microphone may be attached to a separate collar or to a common collar, but in a different housing. The communication between the microphone and the control means is performed wirelessly.

OPERATION

A cow that enters an animal space 2—there may of course be a plurality such animal spaces at a farm—will be identified in a usual manner by means of the transponder 1, when passing the not shown transmitter/receiver. The sensor 4 senses movement of the cow.

Regarding the breathing sensor embodiment, the sensor 4 senses the distance d corresponding to the difference in displacement of the belly of one side the cow.

The control means 5 calculates the movement rate at a plurality of occasions, such that an average value is possible to establish.

Whenever the control means 5 establishes that the movement rate (or the breathing rate and/or the displacement d differs from the average value, the control means 5 sends a signal in order to alert the milker—e.g. by ringing a bell or calling a mobile telephone. Alternatively, during attachment of teatcups by means of a milking robot 6, it may be that the cow runs into a state of panic. This will be apparent either by establishing an increased movement rate of the cow. The milking session may then be interrupted and restarted when the cow has calmed down. Alternatively, the cow may be let out from the milking stall by opening the gate 7.

It is important that if it is suspected or has been established that the cow acts in an abnormal way, it should be possible to check that cow more intensively. This may be performed either by not checking other "normal" cows each time it is identified in order to allow the "abnormal" cow to be checked more often or by separating the cow to an area where more sensors are arranged.

Furthermore, in order to secure an abnormal behaviour or state of health, the control means 5 calculates the movement rate at a another plurality of occasions, such that a new average value is to established and can be compared to the average value of that cow at its normal state.

As an alternative to calculating an average value, it is, of course, possible to set a predetermined value, even though this would be less precise.

It should be noted that also other kinds of sensors may be used within the scope of the invention, such as inductive proximity sensors. Furthermore, the acceleration may be established by the provision of a pendulum or an integrated circuit with a piezo-electric sensor.

It should also be noted that the different kinds of sensors 4 described, may be used in combination to a so called sensor fusion, which creates an overall signal for increasing sensing accuracy.

Of course, the sensors may be situated in order to sense other parts of the animal than the belly, as shown in the figures.

Furthermore, it should be understood that the invention is not restricted to be used in connection with cows but with any milk animal, such as sheep, goats, buffaloes and horses.

What is claimed is:

1. An apparatus for monitoring an animal comprising:
   control means for establishing a movement rate, said control means having sensor means adapted to sense the movement rate of the animal and to establish a value of the movement rate regarding said animal, said control means being adapted to provide a first output signal; and
   an animal related apparatus adapted to perform an animal related operation to the animal, said control means being associated with said animal related apparatus, wherein said animal related apparatus is adapted to perform an action in response to said first output signal, said control means is adapted to at least suspend said animal related operation in case already started and not to initiate said animal related operation in case not started, said sensor means includes a camera associated with said control means for allowing image processing of a received image.

2. An apparatus according to claim 1, characterised in that the value of the movement rate is stored at a plurality of occasions regarding said animal.

3. An apparatus according to claim 2, wherein said control means is adapted to establish an average of the movement rate regarding said animal, outgoing from the stored values.

4. An apparatus according to claim 1, wherein said sensor means is adapted to provide a value of the velocity or acceleration of said movement rate.

5. An apparatus according to claim 1, wherein said sensor means includes time calculating means for establishment of time elapsed during the movement rate of the animal.

6. An apparatus according to claim 1, wherein said sensor means is adapted to sense the amplitude or the frequency of said movement rate.

7. The apparatus of claim 1, wherein said sensor means is further adapted for allowing establishment of the existence of the animal's breathing, said control means being adapted to provide a second output signal, the apparatus further comprising an automatic milking apparatus having a robot arm for performing said animal related operation and said control means being associated with said robot arm.

8. An apparatus according to claim 7, characterised in that said control means is adapted to at least suspend said animal related operation in case already started and not to initiate said animal related operation in case not started.

9. An apparatus according to claim 7, characterised in that said sensor means includes a laser sensor.

10. An apparatus according to claim 7, characterised in that said sensor means includes an ultrasonic sensor.

11. An apparatus according to claim 7, characterised in that said sensor means comprises at least one ultrasonic distance meter, provided in the vicinity of the animal's belly.

12. An apparatus according to claim 7, characterised in that said animal related operation is at least one of inspecting the teats, spraying the teats, cleaning the teats and attaching teat cups to the teats of the animal.

13. An apparatus according to claim 7, wherein identification means is provided, for allowing values of movement rates regarding an identified individual animal to be evaluated.

14. An apparatus according to claim 3, wherein
   said sensor means is adapted to provide a value of the velocity or acceleration of said movement rate;
   said sensor means includes time calculating means for establishment of time elapsed during the movement rate of the animal; and
   said sensor means is adapted to sense the amplitude or the frequency of said movement rate.

15. An apparatus according to claim 8, wherein
   said sensor means includes at least one of a laser sensor, an ultrasonic sensor and an ultrasonic distance meter, provided in the vicinity of the animal's belly;
   said animal related operation is at least one of inspecting the teats, spraying the teats, cleaning the teats and attaching teat cups to the teats of the animal; and
   identification means is provided, for allowing values of rates regarding an identified individual animal to be evaluated.

* * * * *

UNITED STATES PATENT AND TRADEMARK OFFICE
CERTIFICATE OF CORRECTION

PATENT NO.    : 6,418,876 B1  Page 1 of 1
DATED         : July 16, 2002
INVENTOR(S)   : Robert Christopher Hall et al.

It is certified that error appears in the above-identified patent and that said Letters Patent is hereby corrected as shown below:

Column 4,
Line 31, "displacement by" should read -- displacement d by --.

Signed and Sealed this

Fourteenth Day of October, 2003

JAMES E. ROGAN
*Director of the United States Patent and Trademark Office*